United States Patent [19]

Shudo et al.

[11] Patent Number: 5,719,180
[45] Date of Patent: Feb. 17, 1998

[54] CHROMAN DERIVATIVES HAVING VITAMIN E-LIKE ACTIVITIES

[75] Inventors: Koichi Shudo, 9-18, Shimo-takaido 5-chome, Suginami-ku, Tokyo 168; Masashi Akaike, Saitama, both of Japan

[73] Assignee: Koichi Shudo, Tokyo, Japan

[21] Appl. No.: 656,254

[22] PCT Filed: Dec. 6, 1994

[86] PCT No.: PCT/JP94/02046

§ 371 Date: Aug. 12, 1996

§ 102(e) Date: Aug. 12, 1996

[87] PCT Pub. No.: WO95/15957

PCT Pub. Date: Jun. 15, 1995

[30] Foreign Application Priority Data

Dec. 7, 1993 [JP] Japan ................. 5-340012
Jul. 27, 1994 [JP] Japan ................. 6-175231

[51] Int. Cl.$^6$ ................. A61K 31/35; C07D 311/72
[52] U.S. Cl. ................. 514/456; 549/405; 549/408; 549/410
[58] Field of Search ................. 549/405, 408, 549/410; 514/456

[56] References Cited

U.S. PATENT DOCUMENTS 3,789,086  1/1974  Frick et al. ................. 260/345.5

FOREIGN PATENT DOCUMENTS 407198   1/1991  European Pat. Off. .
445827   9/1991  European Pat. Off. .
2 121 750  8/1972  France .
1 204 840  9/1970  United Kingdom .
1 506 076  4/1978  United Kingdom .
93/09777  5/1993  WIPO .

OTHER PUBLICATIONS

Nair et al., Archives of Biochemistry and Biophysics 114, 488–493, 1966.
Slover et al., The Journal of the American Oil Chemists Society, vol. 44, pp. 161–166, Mar. 1967.

*Primary Examiner*—Johann Richter
*Assistant Examiner*—Laura L. Stockton
*Attorney, Agent, or Firm*—Wenderoth, Lind & Ponack

[57] ABSTRACT

Described herein is a chroman derivative represented by the following formula:

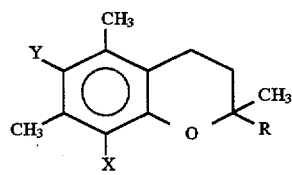

wherein X represents H, —$CH_2OH$, —CHO, —COOH, —$COOCH_3$, —CH=NOH, —$CONH_2$, —$COCH_3$, —CH(OH)$CH_3$, Br, or CN; Y represents a hydroxyl group which may optionally be protected; R represents an alkyl group, alkenyl group, or aralkyl group; provided that, where X is hydrogen atom, R is an alkyl group, alkenyl group, or aralkyl group each having 16 or more carbon atoms; and a vitamin E-like active medicament comprising said derivative as an active ingredient.

28 Claims, No Drawings

CHROMAN DERIVATIVES HAVING VITAMIN E-LIKE ACTIVITIES

This application is a 371 of PCT/JP94/02046 filed Dec. 6, 1994.

TECHNICAL FIELD

The present invention relates to novel chroman derivatives. The chroman derivatives of the present invention have vitamin E activities and antioxidation activity, and are useful as medicaments and ingredients of pharmaceutical composition and the like.

BACKGROUND ART

Vitamin E is known to have various physiological activities such as anti-sterile activity, anti-amyotrophic activity, and anti-hemolytic activity. The physiological activities are considered to be based on its anti-oxidation activity.

Tocopherol and tocotrienol, which are naturally occurring vitamin Es, are structurally characterized in that the benzene ring moiety of the chroman ring is substituted with methyl groups. Such vitamin E derivatives as tocopheramine (J. Am. Chem. Soc., 64, 1082–1084, 1942), tocopherothiol, and thio-tocopherol are known. All of these vitamin E derivatives have methyl groups at 5-, 7-, and 8-positions of the respective chroman rings. A vitamin E derivative having dihydrobenzofran ring, instead of the chroman ring, is also known. The compound also has methyl groups at 4-, 5-, and 7-positions of the dihydrobenzofrun ring, which corresponds to 5-, 6-, and 8-positions of the chroman ring, respectively. Each of the above-described compounds are reported to have vitamin E activities.

Compounds introduced with a hydroxymethyl group or a formyl group at 5-position of a chroman ring (Chemiker-Zeitung, 115, pp. 113–116, 1991). However, no pharmacological activity of these compounds is described in the publication.

DISCLOSURE OF INVENTION

The inventors of the present invention conducted molecular designs to provide vitamin E derivatives having excellent pharmacological activities. As a result of syntheses of various compounds, the inventors found that compounds having a chroman ring, in which a methyl group at 8-position is subjected to an oxidation derivatization or a methyl group at 8-positionn is replaced with a hydrogen atom, had various physiological activities including unique anti-oxidation activity and preventive activity against dysembryoplasia. The present invention was achieved on the basis of these findings.

The present invention thus provides chroman derivatives represented by the following formula (I):

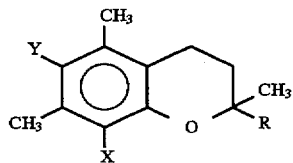

wherein X represents H, —CH$_2$OH, —CHO, —COOH, —COOCH$_3$, —CH=NOH, —CONH$_2$, —COCH$_3$, —CH(OH)CH$_3$, Br, or CN; Y represents a hydroxyl group which may optionally have a protective group; R represents an alkyl group, alkenyl group, or aralkyl group; provided that, where X is hydrogen atom, R is an alkyl group, alkenyl group, or aralkyl group each having 16 or more carbon atoms. According to an embodiment of the present invention, the chroman derivatives wherein Y is a non-protected hydroxyl group are provided.

According to other embodiments of the present invention, there are provided a vitamin E-like active medicament comprising the chroman derivative as an active ingredient; the vitamin E-like active medicament used for therapeutic and preventive treatments of sterility; the vitamin E-like active medicament used for therapeutic and preventive treatments of ischemic disorders; the vitamin E-like active medicament used for therapeutic and preventive treatments of arterial sclerosis; the vitamin E-like active medicament used for activation of microcirculation; the vitamin E-like active medicament used for prevention of fetal abnormality; and the chroman derivatives used as antioxidants.

BEST MODE FOR CARRYING OUT THE INVENTION

In the above formula (I), examples of the alkyl groups represented by R include straight- or branched-chain lower or middle alkyl groups. Examples of the lower alkyl group include straight- or branched-chain alkyl groups having 1 to 5 carbon atoms such as, for example, methyl, ethyl, n-propyl, isopropyl, n-butyl, isobutyl, tert-butyl, n-pentyl, isopentyl, and neopentyl groups. As the middle alkyl group, for example, straight- or branched-chain middle alkyl groups having 6 to about 22 carbon atoms may be used. As the aralkyl group, such groups may be used in which the above-mentioned alkyl groups substituted, preferably at their terminal methyl groups, with one or more phenyl groups. For example, benzyl group and phenethyl group may be used.

Examples of the alkenyl group include those characterized by the above-mentioned alkyl groups introduced with one or more double bonds. Where a lower alkenyl group is used, the number of the unsaturated double bond may preferably be one. However, the position of the double bond is not particularly limited. For example, where an isopentenyl group is used, any one of isopentenyl groups, —CH=CHCH$_2$CH(CH$_3$)$_2$, —CH$_2$CH=CHCH(CH$_3$)$_2$, —CH$_2$CH$_2$CH=C(CH$_3$)$_2$, or —CH$_2$CH$_2$CH$_2$C(CH$_3$)=CH$_2$ may be used. Among the above isopentenyl groups, —CH$_2$CH$_2$CH=C(CH$_3$)$_2$ is preferably used. In addition, where middle alkenyl groups containing repeated isoprene units are used as the middle alkenyl groups, those groups comprising the isoprene repeating units —CH$_2$CH$_2$CH$_2$CH(CH$_3$))— introduced with at least one double bond. The positions of the introduced double bonds are not particularly limited. For example, an alkenyl group represented by —[CH$_2$CH$_2$CH=C(CH$_3$)]n-CH$_3$ (n represents an integer of from 1 to 4) is preferably used.

Among the above-explained alkyl, alkenyl, and aralkyl groups represented by R, alkyl groups are preferably used, and most preferably, middle alkyl groups containing repeated isoprene units such as a group represented by —[(CH$_2$CH$_2$CH$_2$CH(CH$_3$)]n-CH$_3$ (n represents an integer of from 1 to 4) may be used. Where X is a hydrogen atom, R represent one of the above mentioned alkyl, alkenyl and aralkyl groups each having 16 or more carbon atoms. Preferably, an alkyl, alkenyl or aralkyl group having 16 to 22 carbon atoms may be used. Straight- or branched-chain alkyl groups having 16 carbon atoms are particularly preferred. Where Y represents a hydroxyl group having a protective group, any one of hydroxyl protective groups known to those skilled in the art may be used as the protective groups.

3

For example, benzyl, benzoyl, acetyl, trimethylsilyl group and the like may be used.

Among the chroman derivatives of present invention, compounds where X is —CHO group may be prepared by reacting 5,7-dimethyltocopherol, which is prepared according to the method described below as a reference example, with HCN or trimethylsilyl cyanide (TMS-CN). Compounds where X is —$CH_2OH$ can be prepared by the reduction of the above formyl compounds. Compounds where X is —COOH can be prepared by treating 5,7-dimethyl-8-halotocopherol, which is obtained by halogenating the above-described dimethy compounds, with a strong base to prepare its anion, followed by reacting with $CO_2$. In addition, compounds where X is an acyl group can be prepared by Friedel-Crafts acylation using 5,7-dimethyltocopherol as a starting material. The method for preparing the chroman derivatives of the present invention will be further detailed in the following examples.

The chroman derivatives of the present invention have anti-oxidation activity and exhibit vitamin E-like physiological activities, pharmaceutical compositions comprising one or more of the above-mentioned compounds, as one or more active ingredients, are useful as vitamin E-like active medicaments. For example, the vitamin E-like active agents of the present invention are useful for therapeutic and preventive treatments of sterility, therapeutic and preventive treatments of ischemic disorders and arterial sclerosis, and activation of microcirculation.

The route of administration of the vitamin E-like active medicament of the present invention is not particularly limited and they may be administered orally and parenterally. Examples of pharmaceutical formulations suitable for oral administrations include tablets, capsules, powders, fine granules, granules, liquids, and syrups. Examples of pharmaceutical formulations suitable for parenteral administrations include injections, suppositories, inhalants, ointments, and plasters. The vitamin E-like active medicaments of the present invention may be prepared by optionally adding pharmacologically and pharmaceutically acceptable additives. Example of the pharmacologically and pharmaceutically acceptable additives include excipients, disintegrators or disintegrating aids, binders, lubricants, coating agents, coloring agents, diluents, base materials, dissolving agents or dissolving accelerators, isotonizing agents, pH adjusting agents, stabilizers, propellants, tackifiers, and the like.

Pharmaceutical additives, for example, excipients such as glucose, lactose, D-mannitol, starch, and crystalline cellulose; disintegrator or disintegrating aids such as carboxymethyl cellulose, starch, and carboxymethyl cellulose calcium; binders such as hydroxypropyl cellulose, hydroxypropylmethyl cellulose, polyvinylpyrrolidone, and gelatin; lubricants such as magnesium stearate and talc; coating agents such as hydroxypropylmethyl cellulose, saccharose, polyethylene glycol, and titanium oxide; bases such as vaseline, liquid paraffin, polyethylene glycol, gelatin, kaolin, glycerin, purified water, and hard fat; propellants such as fron gases, diethyl ether, and compressed gases; tackifiers such as sodium polyacrylate, polyvinyl alcohol, methyl cellulose, polyisobutylene, and polybutene; and base sheets such as cotton cloth and plastic sheets may be added to the pharmaceutical formulations suitable for oral administrations, and transdermal or transmucosal application. Pharmaceutical additives, for example, dissolving agents or dissolving accelerators such as distilled water for injection, physiological saline, and propylene glycol which can provide aqueous injections or injections prepared by dissolving before use; isotonizing agents such as glucose,

4 sodium chloride, D-mannitol, and glycerin; and pH adjusting agents such as inorganic acids, organic acids, inorganic bases, and organic bases may be added to the pharmaceutical formulations suitable for injections.

The dose of the vitamin E-like active medicaments of the present invention is not particularly limited, which may be suitably chosen depending on, for example, the routes of administrations, ages, body weights, and conditions of patients. For example, the medicament may be administered to an adult in an amount of 1 to 1,000 mg, preferably 1 to 100 mg per day for oral administration. The vitamin E-like active medicaments of the present invention may be administered once or several times a day. Periods of times for the administration may also be chosen depending on, for example, the ages and conditions of patients.

The chroman derivatives of the present invention may also be used as antioxidants. For example, they can be used as antioxidants to prevent oxidation of various components contained in a variety of drugs, cosmetics, food and the like. For such purposes, amounts to be applied may suitably be chosen depending on the purposes, for example, according to an amount of tocopherol ordinarily used in drugs, cosmetics, or food as an antioxidant. When used as antioxidants such as those for drugs or cosmetics, the antioxidants of the present invention may be used in an amount of from 0.1 to 10 mg, for example, based on 1 g of main components.

EXAMPLES

The present invention will be further detailed by examples. However, the scope of the present invention is not limited to these examples.

Example 1

A mixture of 2,6-dimethylhydroquinone (772 mg, 5.59 mmol), $ZnCl_2$ (382 mg, 2.80 mmol, 0.5 eq.), silica gel (777 mg), concentrated hydrochloric acid (4 drops), and carbon tetrachloride (8 ml) was refluxed under argon flow. A solution of $CH_2=CHC(CH_3)_2OH$ (568 mg, 6.59 mmol, 1.2 eq.) in carbon tetrachloride (6 ml) was added dropwise to the mixture over 20 minutes. Then, the mixture was further stirred for 80 minutes at an outer temperature of 110° C. After cooling to room temperature, the reaction mixture was added with dichloromethane (200 ml) and filtered. The filtrate was successively washed with a mixture of 5% NaOH and 1% $Na_2S_2O_4$ (90 ml), water (90 ml), and brine (100 ml). The organic layer was dried over $MgSO_4$ and filtered, and then the solvent was evaporated to give a crude product (1.10 g). After purification by silica gel column chromatography (ethyl acetate:n-hexane=1:5), 907 mg of the desired compound (the compound of formula I where R=$CH_3$ and X=H) was obtained (yield 79%). After recrystallization from n-hexane, colorless needles (m.p. 88° C.) were obtained.

$^1$H-NMR (CDCl$_3$, 60 MHz):

δ 1.28 (6H, s), 1.77 (2H, t, J=6 Hz), 2.11 (3H, s), 2.17 (3H, s), 2.60 (2H, t, J=6 Hz), 4.17 (1H, s), 6.48 (1H, s)

IR (KBr): 3320, 2960, 2920 cm$^{-1}$

Elemental analysis: Calcd. N: 0, C: 75.69, H: 8.80

Found N: 0, C: 75.68, H: 8.92

Example 2

A mixture of 2,6-dimethylhydroquinone (415 mg, 3.00 mmol), $ZnCl_2$ (204 mg, 1.50 mmol, 0.5 eq.), silica gel (415 mg), concentrated hydrochloric acid (3 drops), and carbon tetrachloride (6 ml) was refluxed under argon flow. To this mixture, a solution of $CH_3CH(CH_3)CH_2CH_2CH_2C(CH_3)(OH)CH=CH_2$ (582 mg, 3.72 mmol, 1.2 eq.) in carbon tetrachloride (3 ml) was added dropwise over 20 minutes, and the funnel was washed with carbon tetrachloride (1 ml). Then, the mixture was further stirred at an outer temperature of 115° C. for 1 hour. After cooling to room temperature, the reaction mixture was added with dichloromethane (180 ml) and filtered. The filtrate was successively washed with a mixture (90 ml) of 5% NaOH and 1% $Na_2S_2O_4$, water (90 ml), and brine (90 ml). After the organic layer was dried over $MgSO_4$ and filtered, the solvent was evaporated to give brown oil (943 mg). After purification by silica gel column chromatography (dichloromethane:n-hexane=3:2), the desired compound (the compound of formula I where R=$CH_2CH_2CH_2CH(CH_3)_2$ and X=H) was obtained as pale orange crystals (681 mg, yield 83%). After recrystallization from n-hexane, white granule crystals were obtained (m.p. 46°–47° C.).

$^1$H-NMR (CDCl$_3$, 400 MHz):

δ 0.86 (6H, d, J=6.6 Hz), 1.23 (3H, s), 1.12–1.61 (7H, m), 1.72–1.87 (2H, m), 2.12 (3H, s), 2.18 (3H, s), 2.58 (2H, t, J=6.9 Hz), 4.16 (1H, br.s), 6.47 (1H, s)

Elemental analysis: Calcd. N; 0, C; 78.21, H; 10.21
Found N; 0, C; 78.11, H; 10.29

Example 3

A mixture of 2,6-dimethylhydroquinone (1.50 g, 10.9 mmol), $ZnCl_2$ (739 mg, 5.43 mmol, 0.5 eq.), silica gel (1.50 g), concentrated hydrochloric acid (0.5 ml), and carbon tetrachloride (21 ml) was refluxed under argon flow. To this mixture, a solution of $CH_3CH(CH_3)CH_2CH_2CH_2CH(CH_3)CH_2CH_2CH_2C(CH_3)(OH)CH=CH_2$ (2.96 g, 13.0 mmol, 1.2 eq.) in carbon tetrachloride (12 ml) was added dropwise over 25 minutes and the funnel was washed with carbon tetrachloride (3 ml). Then, the mixture was further stirred at an outer temperature of 115° C. for 1 hour. After cooled to room temperature, the mixture was added with dichloromethane (500 ml) and filtered. The filtrate was successively washed with a mixture (200 ml) of 5% NaOH and 1% $Na_2S_2O_4$, water (200 ml) and brine (200 ml). After the organic layer was dried over $MgSO_4$ and filtered, the solvent was evaporated to give oil (4.46 g). After purification by silica gel column chromatography (dichloromethane:n-hexane=1:1, the desired compound (the compound of formula I where R=$[CH_2CH_2CH_2CH(CH_3)]_2CH_3$ and X=H) was obtained as yellow oil (3.17 g, yield 84%).

$^1$H-NMR (CDCl$_3$, 400 MHz):

δ 0.84 (3H, d, J=6.6 Hz), 0.86 (6H, d, J=6.6 Hz), 1.23 (3H, s), 1.00–1.60 (14H, m), 1.71–1.87 (2H, m), 2.12 (3H, s), 2.18 (3H, s), 2.58 (2H, t, J=6.2 Hz), 4.15 (1H, s), 6.48 (1H, s)

Example 4

A mixture of 2,6-dimethylhydroquinone (1.50 g, 10.9 mmol), $ZnCl_2$ (743 mg, 5.45 mmol, 0.5 eq.), silica gel (1.50 g), concentrated hydrochloric acid (0.5 ml), and carbon tetrachloride (20 ml) was refluxed under argon flow. To this mixture, a solution of isophytol (3.88 g, 13.1 mmol, 1.2 eq.) in carbon tetrachloride (10 ml) was added dropwise over 30 minutes. The mixture was then stirred at an outer temperature of 110° C. for 1 hour. After cooling to room temperature, the reaction mixture was added with dichloromethane and filtered. The dichloromethane layer was successively washed with a mixture of 5% NaOH and 1% $Na_2S_2O_4$, water, and brine. The organic layer was dried over $MgSO_4$ and filtered, and the solvent was evaporated under reduced pressure to give brown oil (5.46 g). After purification by silica gel chromatography (dichloromethane:n-hexane=9:10), the desired compound (the compound of formula I where R=$[CH_2CH_2CH_2CH(CH_3)]_3$—$CH_3$ and X=H) was obtained as colorless oil (2.80 g, yield 62%).

$^1$H-NMR (CDCl$_3$, 400 MHz):

δ 0.83–0.87 (12H, m), 1.23 (3H, s), 1.00–1.62 (21H, m), 1.71–1.87 (2H, m), 2.12 (3H, s), 2.18 (3H, s), 2.58 (2H, t, J=6.9 Hz), 4.15 (1H, s), 6.47 (3H, s)

Example 5

The compound of Example 1 (300 mg) was dissolved in trifluoroacetic acid (10.0 ml), trifluoromethane-sulfonic acid (0.19 ml) was added to the solution under ice-cooling, and then TMS-CN (1.0 ml) under ice cooling, followed by twice addition of TMS-CN with 2 hour interval. After the mixture was allowed to react at room temperature for 24 hours in total, the reaction solution was poured into ice water to carry out hydrolysis, and then the mixture was extracted with dichloromethane. The organic layer was washed with saturated aqueous sodium hydrogen carbonate, dried over $MgSO_4$ and filtered. The filtrate was concentrated under reduced pressure and the residue obtained was purified by silica gel column chromatography. The resulting product (the compound of formula I where R=$CH_3$ and X=CHO) was recrystallized from benzene/n-hexane to give yellow columnar crystals. m.p. 131°–133° C.

$^1$H-NMR (CDCl$_3$, 400 MHz):

δ 1.34 (6H, s), 1.85 (2H, t, J=6.6 Hz), 2.19 (3H, s), 2.48 (3H, s), 2.66 (2H, t, J=6.6 Hz), 4.60 (1H, br), 10.58 (1H, s)

IR (KBr): 3360, 2960, 2920, 1650, 1600 cm$^{-1}$

M $^+$ 234

Elemental analysis: Calcd. N; 0, C; 71.77, H; 7.74
Found N; 0, C; 71.86, H; 7.85

Examples 6 to 8

Using the compounds of Examples 2 to 4, compounds of Examples 6 to 8 were obtained in the same manner as Example 5.

Compound of Example 6 (the compound of formula I where R=$CH_2CH_2CH_2CH(CH_3)_2$ and X=CHO)

Yellow oil $^1$H-NMR (CDCl$_3$, 400 MHz):

δ 0.86 (6H, d, J=6.6 Hz), 1.28 (3H, s), 1.10–1.68 (7H, m), 1.78–1.93 (2H, m), 2.19 (3H, s), 2.48 (3H, s), 2.64 (2H, t, J=7.0 Hz), 4.44 (1H, s), 10.58 (1H, s)

Compound of Example 7 (the compound of formula I where R=$[CH_2CH_2CH_2CH(CH_3)]_2CH_3$ and X=CHO)

Yellow oil $^1$H-NMR (CDCl$_3$, 400 MHz):

δ 0.85 (3H, d, J=6.9 Hz), 0.86 (3H, d, J=6.6 Hz), 1.28 (3H, s) 1.00–1.68 (14H, m), 1.78–1.92 (2H, m), 2.19 (3H, s), 2.48 (3H, s), 2.64 (2H, t, J=6.6 Hz), 4.40 (1H, br.s), 10.58 (1H, s)

Compound of Example 8 (the compound of formula I where R=$[CH_2CH_2CH_2CH(CH_3)]_3CH_3$ and X=CHO)

Pale yellow oil $^1$H-NMR (CDCl$_3$, 400 MHz):

δ 0.85 (12H, m), 1.00–1.69 (21H, m), 1.28 (3H, s), 1.77–1.92 (2H, m), 2.19 (3H, s), 2.48 (3H, s), 2.64 (2H, t, J=6.6 Hz), 4.56 (1H, br.s), 10.58 (1H, s)

Example 9

The compound of Example 5 (100 mg, 0.43 mmol) was dissolved in methanol (3 ml) and stirred on an ice bath. To this solution, an ice cooled solution of $NaBH_4$ (22 mg, 0.57 mmol, 1.3 eq.) in methanol (2 ml) was added dropwise and mixed over 5 minutes under an ice bath. After removing the ice bath, the solution was stirred for 10 minutes at room temperature, and then the reaction was stopped by adding water (5 ml). The methanol was evaporated under reduced pressure, and the residue was extracted with dichloromethane. The organic layer was dried over $MgSO_4$ and filtered, and the solvent was evaporated under reduced pressure to give the desired compound (the compound of formula I where $R=CH_3$ and $X=CH_2OH$) as white powder (98 mg, yield 96%). Recrystallization from benzene/n-hexane gave white powder crystals (m.p. 125° C.).

$^1$H-NMR ($CDCl_3$, 400 MHz):

δ 1.32 (6H, s), 1.83 (2H, t, J=6.6 Hz), 2.13 (3H, s), 2.25 (3H, s), 2.56 (1H, br), 2.64 (2H, t, J=6.6 Hz), 4.26 (1H, s), 4.70 (2H, br.s)

IR (KBr): 3410, 3250, 2960, 2920 cm$^{-1}$

Elemental analysis: Calcd. N; 0, C; 71.16, H; 8.53

Found N; 0, C; 71.38, H; 8.68

Examples 10 to 12

Using the compounds of Examples 6 to 8, compounds of Examples 10 to 12 were obtained in the same manner as Example 9.

Compound of Example 10 (the compound of formula I where $R=CH_2CH_2CH_2CH(CH_3)_2$ and $X=CH_2OH$)

Colorless oil $^1$H-NMR ($CDCl_3$, 400 MHz):

δ 0.87 (6H, d, J=6.6 Hz), 1.12–1.65 (7H, m), 1.26 (3H, s), 1.75–1.90 (2H, m), 2.13 (3H, s), 2.23 (3H, s), 2.61 (2H, t, J=7.0 Hz), 4.49 (1H, br), 4.70 (2H, br.t)

Compound of Example 11 (the compound of formula I where $R=[CH_2CH_2CH_2CH(CH_3)]_2CH_3$ and $X=CH_2OH$)

Colorless oil $^1$H-NMR ($CDCl_3$, 400 MHz):

δ 0.85 (3H, d, J=5.5 Hz), 0.86 (6H, d, J=6.6 Hz), 1.26 (3H, s), 1.01–1.66 (14H, m), 1.74–1.91 (2H, m), 2.13 (3H, s), 2.25 (3H, s), 2.62 (2H, t, J=6.9 Hz), 4.25 (1H, br.s), 4.68 (1H, d, J=12.0 Hz), 4.72 (1H, d, J=12.0 Hz)

Compound of Example 12 (the compound of formula I where $R=[CH_2CH_2CH_2CH(CH_3)]_3CH_3$ and $X=CH_2OH$)

Colorless oil $^1$H-NMR ($CDCl_3$, 400 MHz):

δ 0.83–0.88 (12H, m), 1.00–1.67 (21H, m), 1.26 (3H, s), 1.77–1.92 (2H, m), 2.13 (3H, s), 2.25 (3H, s), 2.62 (2H, T, J=6.9 Hz), 4.25 (1H, br.s), 4.68 (1H, d, J=12.0 Hz), 4.72 (1H, d, J=12.0 Hz)

Example 13

60% NaH (462 mg, 11.5 mmol, 1.2 eq.) was washed several times with n-hexane and suspended in dimethylformamide. A solution of the compound of Example 1 (2.0 g, 9.7 mmol) in dimethylformamide (1.5 ml) was added dropwise to the suspension over 5 minutes with stirring on an ice bath. After completion of the dropwise addition, stirring was continued for 10 minutes, and then benzyl bromide (2.1 g, 12.1 mmol, 1.3 eq.) in dimethylformamide (10 ml) was added. After stirring for 1 hour on an ice bath, the reaction was stopped by adding water. The mixture was extracted with dichloromethane and dried over $MgSO_4$, the solvent was evaporated. Purification by silica gel column chromatography (dichloromethane:n-hexane=2:3) gave the compound where 6-hydroxyl group of the compound of Example 1 was benzylated (2.9 g, yield 88%).

Colorless oil $^1$H-NMR ($CDCl_3$, 400 MHz):

δ 1.31 (6H, s), 1.81 (2H, t, J=7.0 Hz), 2.18 (3H, s), 2.25 (3H, s), 2.60 (2H, t, 7.0 Hz), 4.73 (2H, s), 6.51 (1H, s), 7.34 (1H, t, 7.3 Hz), 7.42 (2H, t, 7.3 Hz), 7.49 (2H, d, J=7.3 Hz)

Examples 14 to 16

By the benzylation of respective 6-hydroxyl groups of the compounds of Examples 2 to 4 in the same manner as Example 13, compounds of Examples 14 to 16 were prepared.

Compound of Example 14

Colorless oil $^1$H-NMR ($CDCl_3$, 400 MHz):

δ 0.87 (6H, d, 6.6 Hz), 1.25 (3H, s), 1.14–1.63 (7H, m), 1.73–1.89 (2H, m), 2.25 (3H, s), 2.58 (2H, t, 7.0 Hz), 4.73 (2H, s), 6.51 (1H, s), 7.34 (1H, t, 7.3 Hz), 7.42 (2H, t, 7.3 Hz), 7.49 (2H, d, J=7.3 Hz)

Compound of Example 15

Colorless oil $^1$H-NMR ($CDCl_3$, 400 MHz):

δ 0.84 (3H, d, 6.6 Hz), 0.86 (6H, d, 6.6 Hz), 1.25 (3H, s), 1.00–1.63 (14H, m), 1.72–1.89 (2H, m), 2.17 (3H, s), 2.24 (3H, s), 2.57 (2H, t, 7.0 Hz), 4.73 (2H, s), 6.51 (1H, s), 7.34 (1H, t, 7.3 Hz), 7.42 (2H, t, 7.3 Hz), 7.49 (2H, d, J=7.3 Hz)

Compound of Example 16

Colorless oil $^1$H-NMR ($CDCl_3$, 400 MHz):

δ 0.83–0.87 (12H, m), 1.25 (3H, s), 1.00–1.62 (21H, m), 1.71–1.87 (2H, m), 2.17 (3H, s), 2.24 (3H, s), 2.57 (2H, t, 7.0 Hz), 4.73 (2H, s), 6.51 (1H, s), 7.34 (1H, t, 7.3 Hz), 7.42 (2H, t, 7.3 Hz), 7.49 (2H, d, J=7.3 Hz)

Example 17

A solution of the compound of Example 13 (1.00 g, 3.37 mmol) in carbon tetrachloride (6 ml) was added to $CF_3CO_2Ag$ (745 mg, 3.37 mmol, 1.0 eq.). A solution of $Br_2$ (0.32 ml, 3.37 mmol, 1.0 eq.) in carbon tetrachloride (6 ml) was added dropwise to the mixture with stirring. After additional stirring for 30 minutes, the reaction mixture was filtered and the filtrate was concentrated under reduced pressure. The residue was purified by silica gel column chromatography (dichloromethane:n-hexane=2:3) to give 8-bromo compound (820 mg, yield 65%).

$^1$H-NMR ($CDCl_3$, 400 MHz):

δ 1.34 (6H, s), 1.79 (2H, t, J=7.0 Hz), 2.14 (3H, s), 2.37 (3H, s), 2.60 (2H, t, J=7.0 Hz), 4.68 (2H, s), 7.32 (1H, t, J=7.3 Hz), 7.38 (2H, t, J=7.3 Hz), 7.46 (2H, d, J=7.3 Hz)

Example 18

A solution of the compound of Example 17 (100 mg, 0.27 mmol) in absolute ether (2.5 ml) was added to 14% n-BuLi (in 0.17 ml of n-hexane, 0.37 mmol, 1.4 eq.). The reaction mixture was stirred for 45 minutes on a dry ice-acetone bath (−70° C.) and then poured to dry ice. After acidification with aqueous 2N HCl, the mixture was extracted with ethyl acetate and washed with brine and water. The organic layer was dehydrated over $MgSO_4$, and the solvent was evaporated under reduced pressure to give a crude product (95 mg). The product was purified by silica gel column chromatography (dichloromethane/n-hexane=2:3 → dichloromethane/ethyl acetate/acetic acid=100:100:1) to give 8-carboxyl compound (46 mg, yield 50%) and the recovered starting material (25 mg, 25%).

$^1$H-NMR ($CDCl_3$, 400 MHz):

δ 1.42 (6H, s), 1.93 (2H, t, J=6.7 Hz), 2.23 (3H, s), 2.58 (3H, s), 2.68 (2H, t, J=6.7 Hz), 4.70 (2H, s), 7.36 (1H, t, J=7.3 Hz), 7.42 (2H, t, J=7.3 Hz), 7.48 (2H, d, J=7.3 Hz), 10.05 (1H, br)

Example 19

The compound of Example 18 (200 mg, 0.59 mmol) was subjected to catalytic reduction in ethanol (80 ml) in the presence of 50 mg of Pd (10% carbon) at room temperature for 1 hour. The Pd—C was removed by filtration of the reaction mixture, and the solvent was evaporated under reduced pressure to give 149 mg of the desired compound (the compound of formula I where $R=CH_3$ and $X=COOH$). Recrystallization from ethanol/benzene gave colorless crystals. m.p. 174.5°–176° C.

$^1$H-NMR ($CD_3OD$, 400 MHz):

δ 1.26 (6H, s), 1.81 (2H, t, J=6.6 Hz), 2.12 (3H, s), 2.15 (3H, s), 2.63 (2H, t, J=6.6 Hz)

Elemental analysis: Calcd. N; 0, C; 67.18, H; 7.25

Found N; 0, C; 66.90, H; 7.26

Examples 20 to 22

By the bromination of the compounds of Examples 14 to 16 in the same manner as Example 17, compounds of Examples 20 to 22 were obtained.

Compound of Example 20

Orange oil $^1$H-NMR ($CDCl_3$, 400 MHz)

δ 0.88 (6H, d, 6.6 Hz), 1.29 (3H, s), 1.13–1.68 (7H, m), 1.76–1.89 (2H, m), 2.15 (3H, s), 2.38 (3H, s), 2.61 (2H, t, J=7.0 Hz), 4.70 (2H, s), 7.34 (1H, t, J=7.3 Hz), 7.42 (2H, t, J=7.3 Hz), 7.49 (2H, d, J=7.3 Hz)

Compound of Example 21

Orange oil $^1$H-NMR ($CDCl_3$, 400 MHz)

δ 0.84 (3H, d, 6.6 Hz), 0.86 (6H, d, 6.6 Hz), 1.29 (3H, s), 1.03–1.68 (14H, m), 1.77–1.90 (2H, s), 2.15 (3H, s), 2.38 (3H, s), 2.61 (2H, t, J=7.0 Hz), 4.70 (2H, s), 7.34 (1H, t, J=7.3 Hz), 7.42 (2H, t, J=7.3 Hz), 7.49 (2H, d, J=7.3 Hz)

Compound of Example 22

Orange oil $^1$H-NMR ($CDCl_3$, 400 MHz)

δ 0.83–0.87 (12H, m), 1.00–1.70 (21H, m), 1.29 (3H, s), 1.75–1.90 (2H, m), 2.15 (3H, s), 2.37 (3H, s) 2.61 (2H, t, J=7.0 Hz), 4.70 (2H, s), 7.34 (1H, t, J=7.3 Hz) 7.42 (2H, t, J=7.3 Hz), 7.49 (2H, d, J=7.3 Hz)

Examples 23 and 24

Compound of Example 23 and its des-benzyl compound, i.e., compound of Example 24 (Y=OH, $R=CH_2CH_2CH_2CH(CH_3)CH_3$, X=COOH), were obtained from the compound of Example 20 in the same manners as Examples 18 and 19.

Compound of Example 23

$^1$H-NMR ($CDCl_3$, 400 MHz)

δ 0.87 (6H, d, 6.6 Hz), 1.18 (2H, q. 14.8, 7.1 Hz), 1.34 (3H, s), 1.35–1.70 (6H, m), 1.83–1.97 (2H, m), 2.21 (3H, s), 2.51 (3H, s), 2.64 (2H, t, J=6.6 Hz), 4.70 (1H, s), 7.37 (1H, t, J=7.1 Hz), 7.41 (2H, t, J=7.2 Hz), 7.48 (2H, d, J=7.2 Hz)

Compound of Example 24

Colorless needles m.p. 125°–126° C. (dichloromethane/n-hexane)

$^1$H-NMR ($CD_3OD$, 400 MHz):

δ 0.86 (6H, d, J=9.1 Hz), 1.16 (2H, q, J=15.4, 7.7 Hz), 1.32 (3H, s), 1.35–1.43 (2H, m), 1.50–1.69 (3H, m), 1.82–1.95 (2H, m), 2.17 (3H, s), 2.44 (3H, s), 2.65 (2H, t, 7.2 Hz)

Elemental analysis: Calcd. N; 0, C; 71.22, H; 8.81

Found N; 0, C; 71.04, H; 8.84

Examples 25 and 26

Compound of Example 25 and its des-benzyl compound, i.e., compound of Example 26 (the compound of formula I where $R=[CH_2CH_2CH_2CH(CH_3)]_2CH_3$, X=COOH), were obtained from the compound of Example 21 in the same manners as Examples 18 and 19.

Compound of Example 25

$^1$H-NMR ($CDCl_3$, 400 MHz)

δ 0.84–0.87 (9H, m), 1.35 (3H, s), 1.08–1.66 (14H, m), 1.86–1.95 (2H, m), 2.21 (3H, s), 2.55 (3H, s), 2.65 (2H, t, J=6.5 Hz), 4.70 (1H, s), 7.37 (1H, t, J=6.9 Hz), 7.41 (2H, t, J=7.0 Hz), 7.48 (2H, t, J=7.0 Hz)

Compound of Example 26

Colorless Oil $^1$H-NMR ($CD_3OD$, 400 MHz):

δ 0.83–0.86 (9H, m), 1.32 (3H, s), 1.12–1.66 (13H, m), 1.85–1.92 (2H, m), 2.18 (3H, s), 2.45 (3H, s), 2.65 (2H, t, 7.2 Hz)

Examples 27 and 28

Compound of Example 27 and its des-benzyl compound, i.e., compound of Example 28 (the compound of formula I where $R=[CH_2CH_2CH_2CH(CH_3)]_3CH_3$, X=COOH), were obtained from the compound of Example 22 in the same manners as Examples 18 and 19.

Compound of Example 27

Colorless oil $^1$H-NMR ($CDCl_3$, 400 MHz):

δ 0.83–0.87 (12H, m), 1.32 (3H, s), 1.00–1.74 (21H, m), 1.84–1.98 (2H, m), 2.22 (3H, s), 2.54 (3H, s), 2.64 (2H, t, J=7.0 Hz), 4.70 (2H, s), 7.33 (1H, t, J=7.3 Hz) 7.42 (2H, t, J=7.3 Hz), 7.48 (2H, d, J=7.3 Hz)

Compound of Example 28

Pale yellow oil $^1$H-NMR ($CDCl_3$, 400 MHz):

δ 0.83–0.87 (12H, m), 1.34 (3H, s), 1.00–1.72 (21H, m), 1.83–1.98 (2H, m), 2.19 (3H, s), 2.50 (3H, s), 2.67 (2H, t, J=7.0 Hz), 4.60 (1H, br.s)

Example 29

$ZnCl_2$ (763 mg, 5.60 mmol) was suspended in 1,2-dichloroethane (3 ml). To this suspension, a solution of $CH_3COCl$ (243 mg, 3.09 mmol) in 1,2-dichloroethane (1.5 ml) was added dropwise and mixed at 0° C. A solution of the compound of Example 1 (238 mg, 1.15 mmol) in 1,2-dichloroethane (2 ml) were added dropwise to the mixture at 0° C. and mixed. The mixture was stirred at room temperature for 2 hours and then a solution of $CH_3COCl$ (97 mg, 1.23 mmol) in 1,2-dichloroethane (1.5 ml) was added dropwise to the mixture and mixed at room temperature. The mixture was further stirred at room temperature for 1 hour and then poured into ice water (70 ml). The mixture was extracted 3 times with dichloromethane (each 40 ml), and the dichloromethane layer was washed with water until it became neutral, and then further washed with brine. The organic layer was dried over $MgSO_4$ and filtered. Then, the solvent was evaporated under reduced pressure to give the compound where a hydroxyl group at 6-position and chroman ring at 8-position were acetylated (337 mg). Purification by silica gel column chromatography (dichloromethane:n-hexane=2:1) gave a purified product (199 mg, yield 59%). Further recrystallization from dichloromethane/n-hexane gave colorless granular crystals (m.p. 96° C.).

$^1$H-NMR ($CDCl_3$, 400 MHz):

δ 1.31 (6H, s), 1.82 (2H, t, J=6.9 Hz), 1.98 (3H, s), 2.01 (3H, s), 2.38 (3H, s), 2.47 (3H, s), 2.62 (2H, t, J=6.9 Hz)

IR (KBr): 2960, 2920, 1760, 1690 cm$^{-1}$

Elemental analysis: Calcd. N; 0, C; 70.32, H; 7.64
Found N; 0, C; 70.43, H; 7.68

Example 30

The above-described compound (52 mg, 0.18 mmol) was dissolved in methanol (2 ml), and an aqueous 2N KOH (0.13 ml, 0.26 mmol, 1.4 eq.) was added, and then the mixture was stirred at room temperature for 1 hour. Methanol was evaporated under reduced pressure and water (5 ml) was added to the residue. 2N HCl (10 ml) was added so as to adjust its pH to 2, and the mixture was extracted 3 times with dichloromethane (each 10 ml). The organic layers were combined and washed with water (10 ml), dried over $MgSO_4$, and then the solvent was evaporated under reduced pressure to give 44 mg (yield 98%) of the desired compounds (the compound of formula I where R=$CH_3$ and X=$COCH_3$). Recrystallization from n-hexane gave colorless needles (m.p. 108° C.).

$^1$H-NMR ($CDCl_3$, 400 MHz):

δ 1.30 (6H, s), 1.81 (2H, t, J=6.9 Hz), 2.10 (3H, s), 2.13 (3H, s), 2.47 (3H, s), 2.63 (2H, t, J=6.9 Hz), 4.37 (1H, br)

Elemental analysis: Calcd. N; 0, C; 72.55, H; 8.12
Found N; 0, C; 72.59, H; 8.24

Example 31

LiAlH$_4$ (10 mg, 0.24 mmol, 2 eq.) was suspended in absolute ether (1 ml) on an ice bath. A solution of the compound of Example 30 (30 mg, 0.12 mmol) in absolute ether (1 ml) was added dropwise to the suspension. The mixture was stirred for 1 hour on the ice bath and additional 1 hour at room temperature. The reaction was stopped by adding water to the reaction mixture, and the mixture was extracted with ether. The extract was dried over $MgSO_4$ and filtered, and then the solvent was evaporated under reduced pressure to give 35 mg of the desired compound (the compound of formula I where R=$CH_3$ and X=$CH(OH)CH_3$) as white crystals. The crystals were recrystallized from ethyl acetate/n-hexane to give 20 mg of colorless columnar crystals (yield 66%, m.p. 134°–135° C.).

$^1$H-NMR ($CDCl_3$, 400 MHz):

δ 1.34 (3H, s), 1.38 (3H, s), 1.50 (3H, d, J=6.6 Hz), 1.84 (2H, t, J=6.6 Hz), 2.11 (3H, s), 2.14 (3H, s), 2.64 (2H, t, J=6.6 Hz), 4.44 (1H, br.s), 4.56 (1H, br.d, J=10.6 Hz), 5.00 (1H, br.s)

Elemental analysis: Calcd. N; 0, C; 71.97, H; 8.86
Found N; 0, C; 72.24, H; 8.97

Example 32

NaH (80 mg, 60% oil dispersion) was washed with n-hexane 3 times, suspended in dimethylformamide (5 ml), and stirred under ice cooling. A solution of the compound of Example 5 (the compound of formula I where R=$CH_3$ and X=CHO, 400 mg, 1.68 mmol) in dimethylformamide (6 ml) was added dropwise to the mixture and stirred for 10 minutes. Then, a solution of benzyl bromide (360 mg, 2.10 mmol, 1.2 eq.) in dimethylformamide (6 ml) was added dropwise to the mixture. The mixture was stirred for 40 minutes on an ice bath and the reaction was stopped by adding water (2 ml). The mixture was extracted with dichloromethane, and the organic layer was dried over $MgSO_4$, and then the solvent was evaporated to give the compound where the hydroxyl group at 6-position was protected by benzyl group (643 mg). The product was purified by silica gel column chromatography (dichloromethane:n-hexane=3:2) to give the desired compound (536 mg, yield 98%). Recrystallization from ethyl acetate/n-hexane gave cream diamondoid crystals (m.p. 61.5°–62° C.).

$^1$H-NMR ($CDCl_3$, 400 MHz):

δ 1.36 (6H, s), 1.87 (2H, t, 7.0 Hz), 2.23 (3H, s), 2.53 (3H, s), 2.64 (2H, t, J=7.0 Hz), 4.69 (2H, s), 7.36 (1H, d, J=7.0 Hz), 7.41 (2H, t, J=7.0 Hz), 7.48 (2H, d, J=7.0 Hz)

Example 33

The compound of the above-described Example 32 was dissolved in methanol (2.5 ml) and added with an aqueous solution (1.5 ml) of hydroxylamine hydrochloride (222 mg, 3.2 mmol, 1.10 eq.). The mixture was heated at an outer temperature of 90° C. for 3 hours and 20 minutes, and then, the reaction mixture was acidified by adding dry ice and extracted with dichloromethane. The organic layer was dried over $Na_2SO_4$ and the solvent was evaporated to give crystals of 8-oxime compound (106 mg, yield 98%). Recrystallization from dichloromethane/n-hexane gave colorless prisms (m.p. 136° C.).

$^1$H-NMR ($CDCl_3$, 400 MHz):

δ 1.32 (3H, s), 1.82 (2H, t, 6.9 Hz), 2.20 (3H, s), 2.46 (3H, s), 2.62 (2H, t, J=6.9 Hz), 4.71 (2H, s), 7.34 (1H, t, J=7.0 Hz), 7.40 (2H, t, J=7.0 Hz), 7.49 (2H, d, J=7.0 Hz), 8.56 (1H, s)

Example 34

The compound of the above-described Example 33 (8-oxime compound, 102 mg, 0.30 mmol) and acetic anhydride (61 mg, 0.60 mmol, 1.2 eq.) were heated for three and a half hours and the reaction mixture was then poured into water. The mixture was extracted with dichloromethane and the organic layer was washed with saturated aqueous $NaHSO_4$ solution. The mixture was dried over $MgSO_4$ and the solvent was evaporated to give orange crystals of 8-cyano compound (101 mg). Purification by silica gel column chromatography (dichloromethane:n-hexane=3:2) gave 94 mg of the desired compound, and further recrystallization from n-hexane gave colorless needles (m.p. 94° C.).

¹H-NMR (CDCl₃, 400 MHz):

δ 1.37 (6H, s), 1.85 (2H, t, 6.9 Hz), 2.21 (3H, s), 2.42 (3H, s), 2.60 (2H, t, J=6.9 Hz), 4.72 (2H, s), 7.36 (1H, t, J=6.9 Hz), 7.41 (2H, t, J=6.9 Hz), 7.46 (2H, d, J=6.9 Hz)

IR (KBr): 2200 cm⁻¹

Example 35

A mixture of the compound of the above-described Example 34 (8-cyano compound, 82 mg, 0.26 mmol), diethylene glycol (2.5 ml), 40% aqueous KOH solution (3.5 ml), and 18-crown-6 ether (206 mg, 0.78 mmol, 1.3 eq.) was stirred at an outer temperature of 135° C. for 2 days. The reaction mixture was neutralized using concentrated hydrochloric acid and extracted with dichloromethane. The organic layer was dried over MgSO₄ and the solvent was evaporated. The residue was purified by silica gel column chromatography (dichloromethane:n-hexane=1:1→ ethyl acetate: dichloromethane=1:5) to afford 8-amide compound as colorless crystals (73 mg, yield 83%).

¹H-NMR (CDCl₃, 400 MHz):

δ 1.32 (6H, s), 1.83 (2H, t, 7.2 Hz), 2.18 (3H, s), 2.36 (3H, s), 2.62 (2H, t, J=7.2 Hz), 4.70 (2H, s), 5.77 (1H, br, s), 5.94 (1H, br, s), 7.35 (1H, t, J=7.1 Hz), 7.41 (2H, t, J=7.1 Hz), 7.48 (2H, d, J=7.1 Hz)

Elemental analysis: Calcd. N; 4.13, C; 74.31, H; 7.42

Found N; 4.41, C; 74.22, H; 7.46

Example 36

The compound of the above-described Example 35 (50 mg, 0.15 mmol) was dissolved in ethanol (25 ml) and subjected to catalytic hydrogenation reduction at room temperature for 1 hour in the presence of Pd—C catalyst (15 mg). Then, the catalyst was removed by filtration and the solvent was evaporated to give 37 mg of the desired compound (the compound of formula I where R=CH₃ and X=CONH₂) as colorless cotton-like crystals (ethyl acetate/n-hexane, m.p. 221° C.).

¹H-NMR (CDCl₃, 400 MHz):

δ 1.31 (6H, s), 1.85 (2H, t, 6.6 Hz), 2.16 (3H, s), 2.21 (3H, s), 2.69 (2H, t, J=6.6 Hz)

IR (KBr): 3340, 3160, 3050, 2950, 2900, 1740, 1660, 1610 cm⁻¹

The compounds obtained by the above-described examples are shown in Table 1 below.

TABLE 1

| Compound No. | X | Y | R |
|---|---|---|---|
| Example 1 | —H | —OH | —CH₃ |
| Example 2 | —H | —OH | —CH₂CH₂CH₂CH(CH₃)₂ |
| Example 3 | —H | —OH | —[CH₂CH₂CH₂CH(CH₃)]₂CH₃ |
| Example 4 | —H | —OH | —[CH₂CH₂CH₂CH(CH₃)]₃CH₃ |
| Example 5 | —CHO | —OH | —CH₃ |
| Example 6 | —CHO | —OH | —CH₂CH₂CH₂CH(CH₃)₂ |
| Example 7 | —CHO | —OH | —[CH₂CH₂CH₂CH(CH₃)]₂CH₃ |
| Example 8 | —CHO | —OH | —[CH₂CH₂CH₂CH(CH₃)]₃CH₃ |
| Example 9 | —CH₂OH | —OH | —CH₃ |
| Example 10 | —CH₂OH | —OH | —CH₂CH₂CH₂CH(CH₃)₂ |
| Example 11 | —CH₂OH | —OH | —[CH₂CH₂CH₂CH(CH₃)]₂CH₃ |
| Example 12 | —CH₂OH | —OH | —[CH₂CH₂CH₂CH(CH₃)]₃CH₃ |
| Example 13 | —H | —OCH₂C₆H₅ | —CH₃ |
| Example 14 | —H | —OCH₂C₆H₅ | —CH₂CH₂CH₂CH(CH₃)₂ |
| Example 15 | —H | —OCH₂C₆H₅ | —[CH₂CH₂CH₂CH(CH₃)]₂CH₃ |
| Example 16 | —H | —OCH₂C₆H₅ | —[CH₂CH₂CH₂CH(CH₃)]₃CH₃ |
| Example 17 | —Br | —OCH₂C₆H₅ | —CH₃ |
| Example 18 | —COOH | —OCH₂C₆H₅ | —CH₃ |
| Example 19 | —COOH | —OH | —CH₃ |
| Example 20 | —Br | —OCH₂C₆H₅ | —CH₂CH₂CH₂CH(CH₃)₂ |
| Example 21 | —Br | —OCH₂C₆H₅ | —[CH₂CH₂CH₂CH(CH₃)]₂CH₃ |
| Example 22 | —Br | —OCH₂C₆H₅ | —[CH₂CH₂CH₂CH(CH₃)]₃CH₃ |
| Example 23 | —COOH | —OCH₂C₆H₅ | —CH₂CH₂CH₂CH(CH₃)₂ |
| Example 24 | —COOH | —OH | —CH₂CH₂CH₂CH(CH₃)₂ |
| Example 25 | —COOH | —OCH₂C₆H₅ | —[CH₂CH₂CH₂CH(CH₃)]₂CH₃ |
| Example 26 | —COOH | —OH | —[CH₂CH₂CH₂CH(CH₃)]₂CH₃ |
| Example 27 | —COOH | —OCH₂C₆H₅ | —[CH₂CH₂CH₂CH(CH₃)]₃CH₃ |
| Example 28 | —COOH | —OH | —[CH₂CH₂CH₂CH(CH₃)]₃CH₃ |
| Example 29 | —COCH₃ | —OCOCH₃ | —CH₃ |
| Example 30 | —COCH₃ | —OH | —CH₃ |
| Example 31 | —CH(OH)CH₃ | —OH | —CH₃ |
| Example 32 | —CHO | —OCH₂C₆H₅ | —CH₃ |
| Example 33 | —CH=NHOH | —OCH₂C₆H₅ | —CH₃ |

TABLE 1-continued

[Chemical structure: chroman derivative with substituents Y, X on aromatic ring bearing two CH3 groups, and R on the pyran ring with CH3]

| Compound No. | X | Y | R |
|---|---|---|---|
| Example 34 | —CN | —OCH$_2$C$_6$H$_5$ | —CH$_3$ |
| Example 35 | —CONH$_2$ | —OCH$_2$C$_6$H$_5$ | —CH$_3$ |
| Example 36 | —CONH$_2$ | —OH | —CH$_3$ |

Test Example 1

Antioxidation activities of the chroman derivatives of present invention were evaluated by measuring inhibitions against a radical-initiated oxidation of methyl linoleate (suppressions of the amount of oxygen consumption, E. Niki et al., J. Biol. Chem., 259, 4177–4182, 1984). Where $R_0$ represents the rate of oxygen consumption in the absence of an antioxidant (mol/l. min); $R_{inh}$ represents the rate of oxygen consumption with the addition of an antioxidant (mol/l. min); $t_{inh}$ represents the duration time of antioxidant activity (min); and M represents the concentration of antioxidant (=60 μM), the following definitions were made:

Antioxidation ratio=$(R_0-R_{inh})/R_0$

Antioxidation activity
=(antioxidation ratio×duration of antioxidation)/M
=$(R_0-R_{inh})t_{inh}/R_0 \cdot M$ The results are shown in Table 2 set out below.

TABLE 2

| Compound | Antioxidation ratio | Duration time (min.) | Antioxidation activity* |
|---|---|---|---|
| Example 9 | 0.61 | 49 | 49.7 |
| Example 12 | 0.58 | 49 | 47.4 |
| Example 5 | 0.37 | >82 | >50.6 |
| Example 8 | 0.36 | >79 | >47.4 |
| Example 19 | 0.58 | >100 | >96.7 |
| Example 28 | 0.55 | >100 | >91.7 |
| Example 1 | 0.61 | 53 | 53.9 |
| Example 4 | 0.61 | 53 | 53.9 |
| Example 30 | 0.48 | 50 | 40.0 |
| Example 36 | 0.32 | >80 | >42.7 |
| α-tocopherol | 0.71 | 43 | 50.9 |
| blank | 0 | 0 | 0 |

*(1/mol) × 10$^4$

Test Example 2

Vitamin E activities of the chroman derivatives of the present invention were examined as follows.

(1) Preparation of vitamin E deficiency pregnant mice

Female Jcl:ICR mice (purchased from Nippon Crea Co., Ltd) were made pregnant and 8 female mice were chosen from each of litters immediately after the birth. Where numbers of female mice did not reach to 8, male mice from the same litter were added up to the total of 8 mice so as to achieve the same lactation conditions. From the 21st day after the birth, only the female mice (F1 mice) were freely fed with vitamin E (VE) deficient feed (purchased from Oriental Yeast Co.,Ltd.). Those female mice fed with vitamin E deficient feed (9-week old) were crossed with newly purchased Jcl:ICR male mice. Pregnancy was determined from the presence or absence of a vaginal plug and the day when a vaginal plug was observed was defined as 0th day of pregnancy. The following experiments were carried out by using those pregnant mice.

(2) Administration of drugs

Vitamin E used as a control drug; and the following chroman derivatives of the present invention:

the compound of Example 4 (X=H, Y=OH, and R=—[CH$_2$CH$_2$CH$_2$CH(CH$_3$)]$_3$CH$_3$);

the compound of Example 12 (X=CH$_2$OH, Y=OH, and R=—[CH$_2$CH$_2$CH$_2$CH(CH$_3$)]$_3$CH$_3$); and the compound of Example 28 (X=COOH, Y=OH, and R=—[CH$_2$CH$_2$CH$_2$CH(CH$_3$)]$_3$CH$_3$)

were used with lard (no addition of vitamin E, purchased from Oriental Yeast Co.,Ltd.) as medium.

The test compounds were added to lard and dissolved by heating at about 40° C. so as to achieve the doses of each of the test compounds being 5 mg/kg body weight and 10 mg/kg body weight. Body weights of the 0th day of pregnancy were used as body weights for determining the dosages. Administration volume was 0.1 ml per 10 g of body weight and administrations were carried out using oral feeding tubes for mice. The control groups, in which test drugs were not administered, were further divided into two groups, i.e., a group where the mice were administered only lard at an amount of 0.1 ml per 10 g of body weight and another group where the mice were administered with neither of drugs nor lard. The administration periods were up to from the 6th day through the 15th day of pregnancy depending on organogenetic periods of mouse embryos. In addition, a control group was further provided for comparison (1 group) where mice were fed with CE-2 (purchased from Japan Crea Co.,Ltd), a normal feed not deficient in vitamin E. The groups administered with drugs and the control groups are summarized below.

TABLE 3

| Group | No. of dams | Feed | Dosage (mg/Kg) |
|---|---|---|---|
| A: Control (Normal Feed) | 16 | CE-2 | — |
| B: Control (Lard administration) | 6 | VE-deficient feed | — |
| C: Control (No administration) | 4 | VE-deficient feed | — |
| D: Vitamin E Administration | 8 | VE-deficient feed | 5 |
| E: Vitamin E Administration | 7 | VE-deficient feed | 10 |

TABLE 3-continued

| Group | No. of dams | Feed | Dosage (mg/Kg) |
|---|---|---|---|
| F: Administration of Compound of Ex. 4 | 8 | VE-deficient feed | 5 |
| G: Administration of Compound of Ex. 4 | 10 | VE-deficient feed | 10 |
| H: Administration of Compound of Ex. 12 | 8 | VE-deficient feed | 5 |
| I: Administration of Compound of Ex. 12 | 8 | VE-deficient feed | 10 |
| J: Administration of Compound of Ex. 28 | 8 | VE-deficient feed | 5 |
| K: Administration of Compound of Ex. 28 | 8 | VE-deficient feed | 10 |

(3) Observation of fetuses and statistical analysis

On the 18th day of pregnancy, the mice were anesthetized with ether and subjected to caesarean section to observe the inside condition of the uteri, and then numbers of implantation, numbers of placental remnant, numbers of absorbed embryo, numbers of alive fetus, and numbers of dead fetus were counted. The results are shown in Tables 4 and 5. In addition, for live fetuses, measurements of body weights, measurements of placental weights, and sex determinations were carried out, and then, the absence or presence of the occurence of physical abnormality were macroscopically examined and counted. The numerical data obtained (body weights and placental weights) were analyzed by t-test, and the frequency data (numbers of implantation, numbers of placental remnant, numbers of absorbed embryo, numbers of alive fetus, numbers of dead fetus, and numbers of the occurence of physical abnormality) were analyzed by chi-square test. In Tables 4 and 5, symbols "a" and "b" represent that significant differences, i.e., $p<0.05$ and $p<0.01$, respectively, were observed between the normal feed control groups and the lard-administered (VE deficient feed) control groups, and symbols "c" and "d" represent that significant differences, i.e., $p<0.05$ and $p<0.01$, respectively, were observed between the lard-administered (VE deficient feed) control groups and the drug-administered groups.

TABLE 4

| Evaluation items/group | A: Normal/feed | B: Lard No drug | Vitamin E | E: Vitamin E |
|---|---|---|---|---|
| No. of dams | 16 | 6 | 4 | 8 | 7 |
| Implantations * | 238 (14.9) | 86 (14.3) | 54 (13.5) | 99 (12.4) | 113 (16.1) |
| Live fetuses** | 226 (14.1) | 80 (13.3) | 51 (12.8) | 98 (12.3) | 111 (15.9) c |
| Placental remnants | 5 (2.1) | 1 (1.2) | 0 | 0 | 0 |
| Absorptions (%) | 5 (2.1) | 1 (1.2) | 2 (3.7) | 1 (1.0) | 0 |
| Dead fetuses (%) | 2 (0.8) | 4 (4.7) | 1. (1.9) | 0 | 2 (1.8) |
| Alive fetuses | | | | | |
| Sex ratio (male/female) | 1.1 | 0.9 | 0.9 | 1.1 | 1.0 |
| Body weight (male) | 1.56 | 1.34 b | 1.27 | 1.52 c | 1.42 |
| Body weight (female) | 1.48 | 1.27 b | 1.24 | 1.39 c | 1.33 |
| Placental weight (mg) | 111 | 92 b | 94 | 95 | 97 |
| No. of abnormal fetuses(%) | 1 (0.4) | 11 (13.8) b | 14 (27.5) | 1 (1.0) d | 4 (3.6) c |
| Exencephaly (%) | 1 (0.4) | 10 (12.5) b | 13 (25.5) | 1 (1.0) d | |
| Macroglossia (%) | 1 (0.4) | 10 (12.5) b | 13 (25.5) | 1 (1.0) d | |
| Open eyelid (%) | 1 (0.4) | 1 (1.3) | 1 (2.0) | — | 1 (0.9) |
| Cleft palate (%) | — | 2 (2.5) | 1 (2.0) | — | 1 (0 9) |
| Ano(micro)phthalmia (%) | — | 1 (1.3) | — | — | — |
| Kinny tail (%) | — | 1 (1.3) | 2 (3.9) | — | 1 (0.9) |
| Cleft lip (%) | — | — | — | — | — |
| Anomaly of tail (%) | — | — | — | — | — |
| Umbilical hernia (%) | — | — | — | — | 1 (0.9) |

*Parenthesized numbers indicate an average number of implantations per a dam.
**Parenthesized numbers indicate an average number of alive fetuses per a dam.

TABLE 5

| Evaluation items/group | F: Example 4 | G: Example 4 | H: Example 12 | I: Example 12 | J: Example 28 | K: Example 28 |
|---|---|---|---|---|---|---|
| No. of dams | 8 | 10 | 8 | 8 | 8 | 8 |
| Implantation* | 99 (12.4) | 142 (14.2) | 122 (15.3) | 115 (14.4) | 122 (15.3) | 116 (14.5) |
| Live fetuses** | 92 (11.5) | 132 (13.2) | 111 (13.9) | 112 (14.o) | 116 (14.5) | 107 (13.4) |
| Placental remnants (%) | 0 | 1 (0.7) | 9 (7.4) | 1 (0.9) | 1 (0.8) | 2 (1.7) |
| Absorptions (%) | 0 | 7 (4.9) | 2 (1.6) | 2 (1.7) | 4 (3.3) | 4 (3.4) |
| Dead fetuses (%) | 2 (2.o) | 2 (1.4) | 0 | 0 | 1 (0.8) | 3. (2.6) |
| Alive fetuses | | | | | | |
| Sex ratio (male/female) | 0.7 | 0.6 | 0.9 | 1.2 | 1.0 | 1.0 |
| Body weight (male) | 1.57 c | 1.43 | 1.49 d | 1.48 c | 1.41 | 1.49 c |
| Body weight (female) | 1.51 d | 1.33 | 1.40 d | 1.45 c | 1.35 | 1.43 c |
| Placental weight (mg) | 107 | 97 | 111 d | 103 | 96 | 105 |
| No. of abnormal features (%) | 3 (3.3) c | 12 (9.1) | 1 (0.9) d | 0 d | 5 (4.3) c | 3..(2.B) c |

TABLE 5-continued

| Evaluation items/group | F: Example 4 | G: Example 4 | H: Example 12 | I: Example 12 | J: Example 28 | K: Example 28 |
|---|---|---|---|---|---|---|
| Exencephaly (%) | — | 3 (2.3) d | 2 (1.7) d | 3 (2.8) c | | |
| Macroglossia (%) | 2 (1.7) d | 2 (1.9) d | | | | |
| Open eyelid (%) | — | 2 (1.5) | — | 1 (0.9) | | |
| Cleft palate (%) | 1 (1.1) | 9 (6.8) | 1 (0.9) | — | 3 (2.6) | — |
| Ano(micro)phthalmia (%) | — | 2 (1.5) | — | | | |
| Kinky tail (%) | 1 (1.1) | | | | | |
| Cleft lip (%) | — | 1 (0.8) | — | | | |
| Anomaly of tail (%) | — | 1 (0.8) | — | | | |
| Umbilical hernia (%) | 1 (1.1) | — | — | — | — | — |

As shown in the above tables, body weights of the fetuses and placental weights of the vitamin E deficient feed control groups were significantly decreased as compared to the normal feed control group, and the frequency of occurrences of physical abnormality was significantly high. In contrast to those vitamin E deficient control groups, body weights of fetuses and placental weight were recovered in both of the groups administered with vitamin E or the chroman derivatives of the present invention, and frequencies of occurrences of physical abnormality were also significantly decreased in almost all of the groups. Among them, the compound of Example 12 of the present invention exhibited higher activities than vitamin E. From the foregoing results, it is apparent that the chroman derivatives of the present invention have vitamin E-like physiological activities and are useful for prevention of fetal abnormality.

Industrial Applicability

The chroman derivatives of the present invention have antioxidation activity and exhibit vitamin E-like activities such as prevention of fetal abnormality, and thus they are useful as medicaments and antioxidants.

What is claimed is:

1. A chroman derivative represented by the following formula:

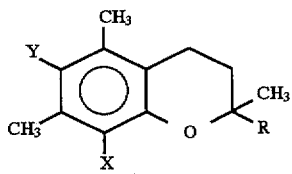

wherein X represents —CH$_2$OH, —COOH, —COOCH$_3$, —CH=NOH, —CONH$_2$, —COCH$_3$, —CH(OH)CH$_3$, Br, or CN; Y represents a hydroxyl group which may optionally be protected; and R represents an alkyl group.

2. The chroman derivative according to claim 1, wherein Y is an unprotected hydroxyl group.

3. The chroman derivative according to claim 1, wherein X is —CH$_2$OH, Y is —OH and R is an alkyl group.

4. The chroman derivative according to claim 1, wherein X is —Br, Y is a protected hydroxyl group and R is an alkyl group.

5. The chroman derivative according to claim 1, wherein X is —COOH, Y is a hydroxyl group which may optionally be protected, and R is an alkyl group.

6. The chroman derivative according to claim 1, wherein X is —COCH$_3$, Y is a hydroxyl group which may optionally be protected, and R is an alkyl group.

7. The chroman derivative according to claim 1, wherein X is —CH(OH)CH$_3$, Y is hydroxyl group and R is an alkyl group.

8. The chroman derivative according to claim 1, wherein X is —CH=NOH, Y is a protected hydroxyl group and R is an alkyl group.

9. The chroman derivative according to claim 1, wherein X is —CN, Y is a protected hydroxyl group and R is an alkyl group.

10. The chroman derivative according to claim 1, wherein X is —CONH$_2$, Y is a hydroxyl group which may optionally be protected, and R is an alkyl group.

11. The chroman derivative according to claim 1, wherein the protected hydroxyl group is —OCH$_2$C$_6$H$_5$.

12. The chroman derivative according to claim 1, wherein R is an alkyl group selected from the group consisting of —CH$_3$, —CH$_2$CH$_2$CH$_2$CH(CH$_3$)$_2$, —[CH$_2$CH$_2$CH$_2$CH(CH$_3$)]$_2$CH$_3$ and —[CH$_2$CH$_2$CH$_2$CH(CH$_3$)]$_3$CH$_3$.

13. A composition comprising the chroman derivative according to claim 1 and a pharmaceutically acceptable additive.

14. A composition comprising the chroman derivative according to claim 2 and a pharmaceutically acceptable additive.

15. A composition comprising the chroman derivative according to claim 3 and a pharmaceutically acceptable additive.

16. A composition comprising the chroman derivative according to claim 4 and a pharmaceutically acceptable additive.

17. A composition comprising the chroman derivative according to claim 5 and a pharmaceutically acceptable additive.

18. A composition comprising the chroman derivative according to claim 6 and a pharmaceutically acceptable additive.

19. A composition comprising the chroman derivative according to claim 7 and a pharmaceutically acceptable additive.

20. A composition comprising the chroman derivative according to claim 8 and a pharmaceutically acceptable additive.

21. A composition comprising the chroman derivative according to claim 9 and a pharmaceutically acceptable additive.

22. A composition comprising the chroman derivative according to claim 10 and a pharmaceutically acceptable additive.

23. A composition comprising the chroman derivative according to claim 11 and a pharmaceutically acceptable additive.

24. A composition comprising the chroman derivative according to claim 12 and a pharmaceutically acceptable additive.

25. A method for treating sterility, which comprises administering to a patient in need thereof a therapeutically effective amount of the chroman derivative according to claim 1.

26. A method for treating ischemic disorders, which comprises administering to a patient in need thereof a therapeutically effective amount of the chroman derivative according to claim 1.

27. A method for treating arterial sclerosis, which comprises administering to a patient in need thereof a therapeutically effective amount of the chroman derivative according to claim 1.

28. A method for activation of microcirculation, which comprises administering to a patient in need thereof a therapeutically effective amount of the chroman derivative according to claim 1.

* * * * *